(12) United States Patent
Caveney et al.

(10) Patent No.: US 10,421,607 B2
(45) Date of Patent: Sep. 24, 2019

(54) CRYOGENIC FREEZER

(71) Applicants: Brooks Automation, Inc., Chelmsford, MA (US); Chart Inc., Garfield Heights, OH (US)

(72) Inventors: Robert T. Caveney, Nashua, NH (US); Frank Hunt, Shrewsbury, MA (US); Lingchen Sun, Milford, MA (US); Julian D. Warhurst, Portsmouth, RI (US); Bruce S. Zandi, Lexington, MA (US); Jeffrey S. Brooks, Jasper, GA (US)

(73) Assignees: Brooks Automation, Inc., Chelmsford, MA (US); Chart Inc., Garfield Heights, OH (US)

( * ) Notice: Subject to any disclaimer, the term of this patent is extended or adjusted under 35 U.S.C. 154(b) by 518 days.

(21) Appl. No.: 15/085,630

(22) Filed: Mar. 30, 2016

(65) Prior Publication Data
US 2016/0289000 A1    Oct. 6, 2016

Related U.S. Application Data

(60) Provisional application No. 62/140,160, filed on Mar. 30, 2015.

(51) Int. Cl.
*B65G 1/04* (2006.01)
*F25D 3/10* (2006.01)
(Continued)

(52) U.S. Cl.
CPC .......... *B65G 1/045* (2013.01); *A01N 1/0236* (2013.01); *A01N 1/0257* (2013.01);
(Continued)

(58) Field of Classification Search
CPC ........ B65G 1/045; B65G 1/0464; B65G 1/06; B65G 1/10; F25D 3/105; F25D 3/11;
(Continued)

(56) References Cited

U.S. PATENT DOCUMENTS

| 5,233,844 A | 8/1993 | Knippscheer et al. |
| 5,921,102 A * | 7/1999 | Vago ................. F25D 25/00 62/266 |

(Continued)

FOREIGN PATENT DOCUMENTS

| CH | 114763 (A) | 4/1926 |
| EP | 2492663 A2 * | 2/2011 |

(Continued)

OTHER PUBLICATIONS

Translation of EP 2492663A2.*
(Continued)

*Primary Examiner* — Elizabeth J Martin
(74) *Attorney, Agent, or Firm* — Hamilton, Brook, Smith & Reynolds, P.C.

(57) ABSTRACT

A configurable cryogenic storage device has a freezer and a rack carrier positioned inside of the freezer. The freezer includes a bearing and a drive shaft though the freezer, the drive shaft being coupled to the rack carrier inside the freezer and adapted to be coupled to a motor assembly. The rack carrier rests on the bearing in a manual rotation configuration and hangs from the drive shaft when the motor is connected. Coupling the drive shaft to the motor assembly lifts the rack carrier and decouples the bearing and enables automated rotation of the rack carrier by the motor. The rack carrier includes rack-mounting features holding a plurality of sample storage racks. The sample storage racks hang from the rack carrier and the rack-mounting features precisely position the end of each sample storage rack.

22 Claims, 19 Drawing Sheets

(51) Int. Cl.
  *F25D 25/02*   (2006.01)
  *A01N 1/02*   (2006.01)
  *F25D 25/04*   (2006.01)
  *G01N 35/00*   (2006.01)
  *G01N 35/04*   (2006.01)

(52) U.S. Cl.
  CPC ........... *B65G 1/0464* (2013.01); *F25D 3/105* (2013.01); *F25D 25/02* (2013.01); *F25D 25/04* (2013.01); *F25D 2400/38* (2013.01); *G01N 2035/00435* (2013.01); *G01N 2035/0425* (2013.01)

(58) Field of Classification Search
  CPC ..... F25D 29/011; F25D 2400/38; G01N 1/42; A01N 1/0257
  See application file for complete search history.

(56) References Cited

U.S. PATENT DOCUMENTS

| | | |
|---|---|---|
| 6,393,847 B1 | 5/2002 | Brooks et al. |
| 2003/0233842 A1 | 12/2003 | Junca et al. |
| 2010/0253190 A1 | 10/2010 | Li et al. |
| 2012/0134898 A1 | 5/2012 | Malin |
| 2016/0288999 A1 | 10/2016 | Caveney et al. |

FOREIGN PATENT DOCUMENTS

| | | |
|---|---|---|
| EP | 2492663 A2 | 2/2012 |
| EP | 2492663 A2 | 8/2012 |
| WO | WO 2016/160984 A1 | 10/2016 |
| WO | WO 2016/160986 A2 | 10/2016 |

OTHER PUBLICATIONS

Invitation to Pay Additional Fees including Communication Relating to Results of Partial International Search for Int'l Application No. PCT/US2016/025002, "Automated Cryogenic Storage System," dated Jul. 11, 2016.

Invitation to Pay Additional Fees including Communication Relating to Results of Partial International Search for Int'l Application No. PCT/US2016/025004, "Cryogenic Freezer," dated Jul. 15, 2016.

Notification and Transmittal of the International Search Report and the Written Opinion of the International Searching Authority for Int'l Application No. PCT/US2016/025002, "Automated Cryogenic Storage System," dated Sep. 1, 2016.

Notification and Transmittal of the International Search Report and the Written Opinion of the International Searching Authority for Int'l Application No. PCT/US2016/025004, "Cryogenic Freezer," dated Sep. 30, 2016.

Notification Concerning Transmittal of Int'l Preliminary Report on Patentability for Int'l Application No. PCT/US2016/025004, "Cryogenic Freezer," dated Oct. 12, 2017.

Notification Concerning Transmittal of Int'l Preliminary Report on Patentability for Int'l Application No. PCT/US2016/025002, "Automated Cryogenic Storage System," dated Oct. 12, 2017.

* cited by examiner

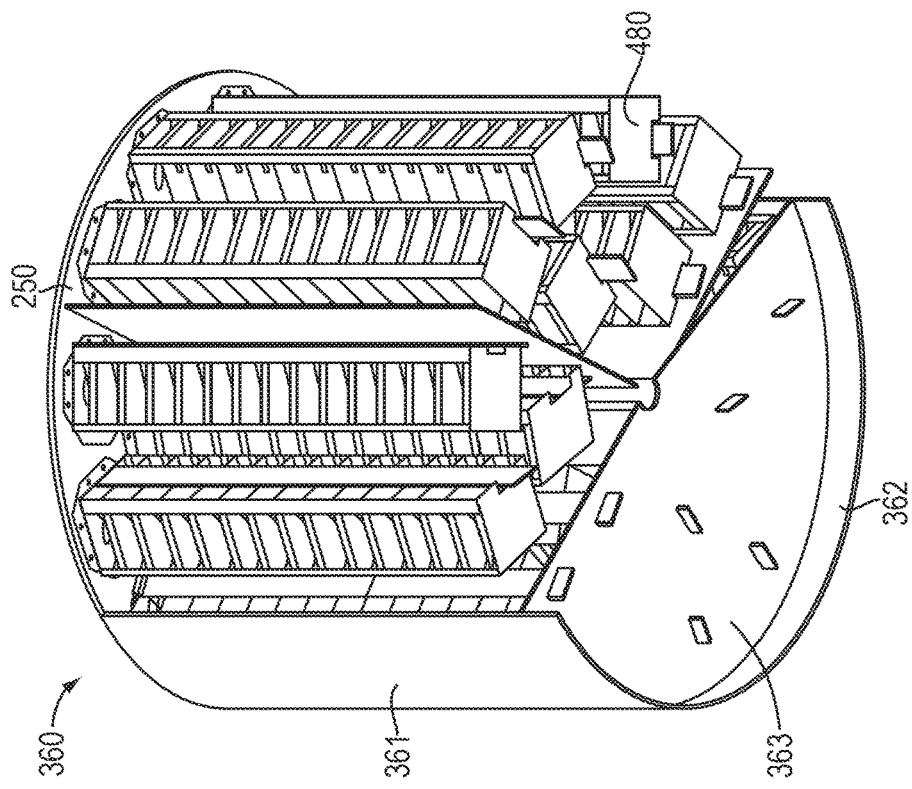
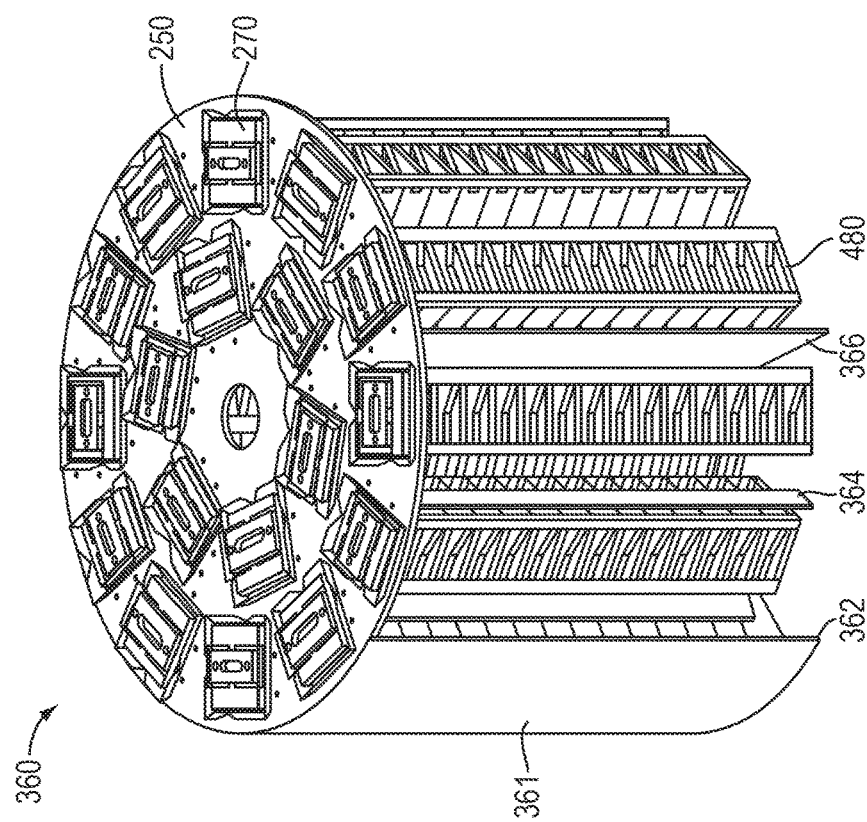
FIG. 5B
FIG. 5A

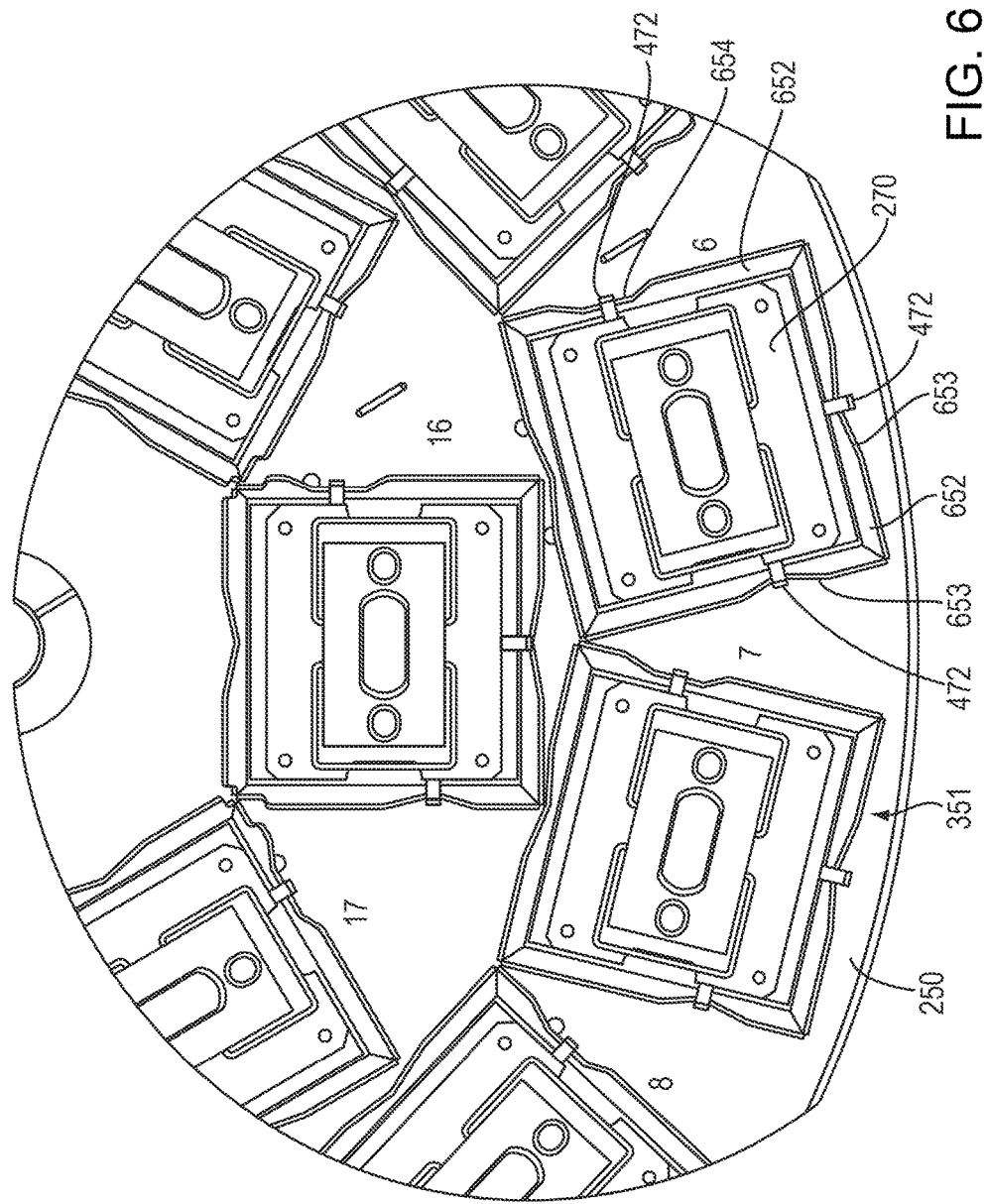

CRYOGENIC FREEZER

RELATED APPLICATION(S)

This application claims the benefit of U.S. Provisional Application No. 62/140,160, filed on Mar. 30, 2015. The entire teachings of the above application is incorporated herein by reference.

BACKGROUND

Cryopreservation is a process essential to maintaining the integrity of biological substances over extended periods of storage. At sufficiently low temperatures, all chemical processes and biological functions of such substances are effectively halted, allowing them to be stored safely over nearly any length of time. A cryogenic storage freezer enables such storage by providing an insulated and controlled cryogenic environment to accommodate a number of biological or other samples. In typical storage freezers, samples are loaded into racks or trays, each of which hold several samples. The racks or trays are manually removed from the cryogenic environment of the freezer, presenting the rack or tray to a user for removing samples from, or adding samples to, the storage freezer.

SUMMARY OF THE INVENTION

An example embodiment of the present invention is a cryogenic storage device comprising a freezer containing a cryogenic environment and a port enabling access to the cryogenic environment through a top portion of the freezer. A rotating rack carrier inside the freezer includes a plurality of rack-mounting features configured to accept sample storage racks. The rack carrier enables the sample storage racks to be removed manually through the port and the rack carrier can be reconfigured to be rotated by a motor and allow the sample storage racks to be retrieved by a retrieval module coupled with the freezer. The freezer includes a bearing having a rotating bearing member coupled with the rack carrier and a stationary race coupled to the freezer. For manual operation, the bearing is configured to support the rack carrier when the stationary race is coupled with the rotating bearing member. The freezer also includes a shaft interface providing a drive shaft though at least a portion of the freezer. To enable automated rotation, the drive shaft has an exterior portion configured to be coupled to a motor and an interior portion coupled to the rack carrier. To reconfigure the freezer, the drive shaft enables vertical translation of the rack carrier to decouple the rotating bearing member from the stationary race. The drive shaft is configured to support the rack carrier when the rotating bearing member is decoupled from the stationary race.

In some embodiments, the sample storage racks hang from the rack-mounting features. The drive shaft coupling with the motor may lift the rotating bearing off of the stationary race and enables the motor to support and level the rack carrier via the drive shaft.

The cryogenic storage device may include a manual rotation configuration and an automated rotation configuration where the rack carrier rests on the rotating bearing in the manual rotation configuration and the rack carrier hangs from the drive shaft coupled to the motor in the automated rotation configuration. Coupling the drive shaft to the motor lifts the rack carrier off of the rotating bearing and transitions the configurable cryogenic storage device from the manual rotation configuration to the automated rotation configuration. In some embodiments, in the automated rotation configuration, the motor supports the weight of the rack carrier via the drive shaft. The rack-mounting features may be coupled to the interior end of the dive shaft, the rack-mounting features supporting the rack carrier.

In some embodiments, the exterior end of the drive shaft includes threads adapted to screw the drive shaft into corresponding threads of the motor assembly, and threading the drive shaft into the corresponding threads of the motor assembly lifts the rack carrier off the bearing.

In some embodiments, the freezer further includes a volume of cryogenic liquid with a lower portion the rack carrier extending into the volume of cryogenic liquid. The top plate being in thermal contact with the lower portion enables the rack-mounting features to conduct heat into the volume of cryogenic liquid and form a cooled thermal mass above the sample storage racks.

In some embodiments, the rotating bearing may be a spherical bearing comprising a spherical feature and a corresponding running surface surrounding a portion of the surface of the spherical feature, the spherical feature may be integrated into the drive shaft and the corresponding running surface may be coupled to the freezer, and coupling the drive shaft to the motor lifts and separates the spherical feature from the corresponding running surface.

In some embodiments, an exterior surface of the top portion of the freezer includes three mounting points adapted to secure the motor to the freezer. The mounting features support the weight of the motor and the rack carrier when the configurable cryogenic storage device is in the automated configuration. The three mounting points may enable leveling of the motor and rack carrier.

In some embodiments an exterior surface of the top portion of the freezer includes at least one mounting feature adapted to secure a retrieval module, the retrieval module is configured to access the freezer and engage a selected one of the plurality of sample storage racks in the rack carrier and elevate the selected one of the sample storage racks through the door and into the retrieval module.

In some embodiments, each sample storage rack includes protruding pins and each rack-mounting feature, which may be integrated into a top plate further comprises corresponding grooves adapted to accept each pin. In some embodiments, each corresponding opening of the plurality of rack-mounting feature includes guide fins surrounding the corresponding opening to guide a bottom end of one of the plurality of sample storage racks when the sample storage rack is lowered through the rack-mounting features or the corresponding openings in the top plate having the rack-mounting features. In some embodiments, the guide fins surrounding each corresponding opening include the corresponding grooves. When accepted, the pins and corresponding grooves constrain the sample storage rack in three dimensions.

Another example embodiment of the present invention is a cryogenic storage device having a freezer and a door enabling access to the cryogenic environment through a top portion of the freezer. The freezer includes a rotating bearing and a shaft interface providing a drive shaft though the freezer, the drive shaft having an exterior end adapted to be coupled to a motor and an interior end inside the freezer, a volume of cryogenic fluid inside the freezer, the volume of cryogenic fluid pooling on a bottom surface of the inside of the freezer, and a rack carrier positioned inside of the freezer holding a plurality of sample storage racks. The rack carrier includes a top plate with a plurality of rack-mounting features, with each of the rack-mounting features adapted to accept a sample storage rack through a corresponding opening in the top plate. A lower portion the rack carrier extends into the volume of cryogenic liquid. The top plate is in thermal contract with the cryogenic fluid via the lower portion of the rack carrier and the top plate conducts heat into the volume of cryogenic liquid to form a thermal mass above the sample storage racks.

Yet another example embodiment of the present invention is a method of converting a manual operation freezer into an automated operation freezer, the method includes, providing a freezer having a drive shaft though a top portion of the freezer and a rack carrier positioned inside of the freezer, the rack carrier resting on a bearing and adapted to be supported by the drive shaft, attaching a motor to an exterior surface of the top portion of the freezer, lifting the rack carrier off the rotating bearing using the drive shaft, the lifting causing the rack carrier to be supported by the drive shaft, and securing the drive shaft to the motor.

In some embodiments, the drive shaft includes a threaded end, and lifting the rack carrier off the rotating bearing using the drive shaft may include threading the threaded end of the drive shaft onto corresponding threads of the motor assembly, thus lifting the rack carrier off of the rotating bearing. Threading the threaded end of the drive shaft onto corresponding threads of the motor assembly may include manually rotating the rack carrier through a door in the top portion of the freezer.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 5A-B are illustrations of a rack carrier and top plate with the top plate securing a plurality of sample storage racks in accordance with aspects of the disclosed embodiment.

FIG. 6 is an illustration of the top plate of and integrated rack-mounting features of FIG. 5A showing interface between pins on the rack and the rack-mounting features in accordance with aspects of the disclosed embodiment.

DETAILED DESCRIPTION OF THE INVENTION

A description of example embodiments of the invention follows.

Figure 1:
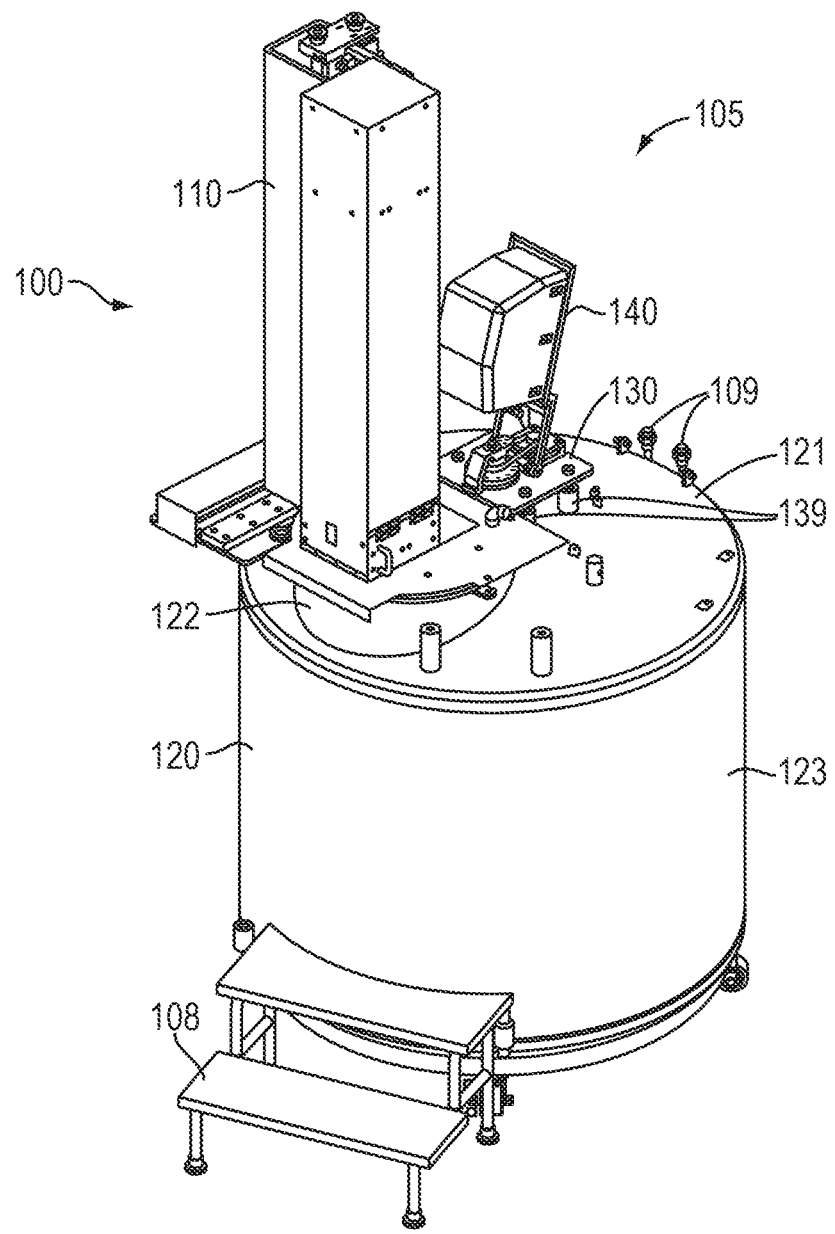
FIG. 1 is an illustration of a configurable cryogenic storage device in accordance with aspects of the disclosed embodiment.

FIG. 1 is an illustration of a configurable cryogenic storage device in accordance with aspects of the disclosed embodiment. FIG. 1 shows a configurable cryogenic storage device 100 comprising a freezer 120 and an automation system 105 having a retrieval module 110, a rotation motor assembly 130, and a freezer door 140 mounted to the freezer 120. The freezer 120 includes a freezer cover 121 and an external wall 123. In the illustrated embodiments, freezer 120 is a cylindrical vessel; however, the freezer can have any shape such as, for example, a rectangular box. In some preferred embodiments, freezer 120 includes an external wall or shell separated from an inner wall or shell by a vacuum insulated space (e.g., a Dewar vessel). The exterior of the freezer cover 121 includes assembly mounts 139 which enable attachment of the motor assembly 130. Cryogenic refrigerant ports 109 ingress and egress to carry a cryogenic refrigerant such as, for example, liquid nitrogen, to and from an inner chamber of the freezer 120. Finally, optional stairs 108 positioned in front of the freezer 120 and near the retrieval module 110 allow an operator to access the retrieval module 110.

In operation, the freezer 120 maintains a cryogenic environment in an inner chamber with a plurality of sample storage racks (not shown). The retrieval module 110 accesses the inner chamber of the freezer 120 though an access port 122 in the freezer cover 121 and retrieves one of the sample storage racks (not shown). To enable the retrieval module 110 to retrieve any sample storage racks in the freezer 120, the sample storage racks are stowed on a rack carrier (not shown in FIG. 1), which may be, for example, a rotatable drum, inside the freezer 120 and the motor assembly 130 controls the rotation of the rack carrier to position a given sample storage rack under the retrieval module 110.

Figure 2B:
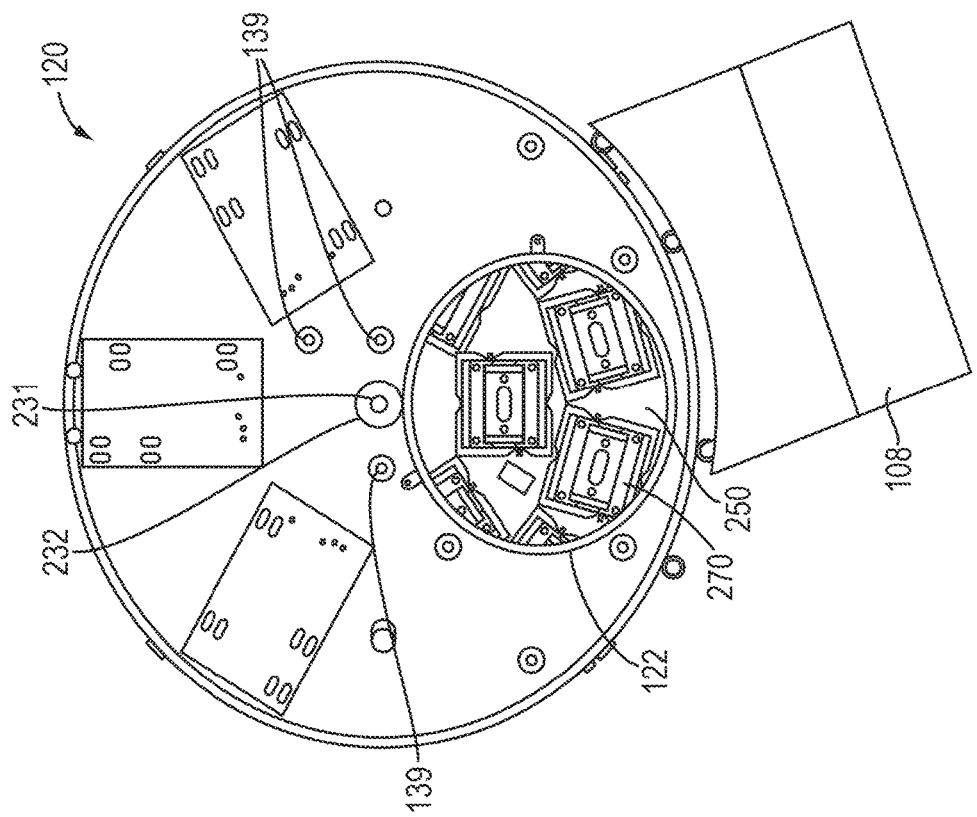
FIGS. 2A-B are illustrations of a cryogenic storage dewar in accordance with aspects of the disclosed embodiment.
Figure 2A:
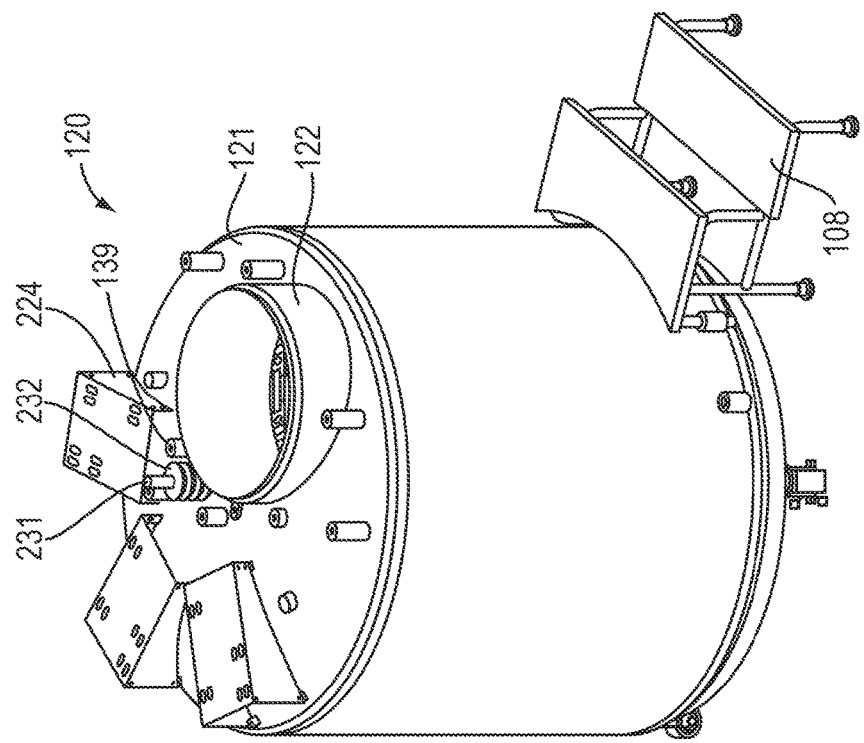

FIGS. 2A-B are illustrations of a cryogenic storage freezer in accordance with aspects of the disclosed embodiment. FIG. 2A shows the cryogenic storage freezer 120 configured for manual access. When configured for manual access, also referred to as in an automation-ready configuration, the freezer 120 lacks the retrieval module 110, motor assembly 130, and automated door 140 (as shown in FIG. 1). Instead, the freezer cover 121 includes mounting racks 224 configured to secure the retrieval module 110, and a drive shaft 231, covered by seal 232, protruding from the cover 121 with mounting studs positioned to secure a motor assembly to the freezer cover 121 for coupling with the drive shaft 231. The access port 122 of the freezer 120 is configured to accept a standard circular cryogenic freezer door (not shown). Seal 232 helps, for example, to prevent moisture from entering the freezer and to keep cold gas from escaping the freezer. In some embodiments, drive shaft 231 is constructed of a low thermally conductive material to minimize transmission of heat into the freezer.

FIG. 2B is a top-down view of the freezer 120 of FIG. 2A. FIG. 2B shows the top plate 250 of a rack carrier (shown in FIG. 3 as 360) positioned inside the freezer 120 through the access port 122 of the freezer cover 121. A rack carrier (shown as a rotatable drum) inside of the freezer 120 is configured to hold a plurality of sample storage racks and rotate inside of the freezer 120 to allow access to each sample storage rack though the access port 122. The precise positioning of the sample storage racks 480 in the top plate 250 of the rack carrier allows a retrieval module 110 to be attached to the freezer 120 and accurately access the position of each sample storage rack 480 by rotating the top plate 250 via the drive shaft 231. In manual operation, a user standing on the stairs 108 may reach through the access port 122 and manually rotate the top plate 250 to present a desired sample storage rack 480 to the user and allow the user to retrieve the sample storage rack by pulling the sample storage rack through the access port 122.

Figure 3:
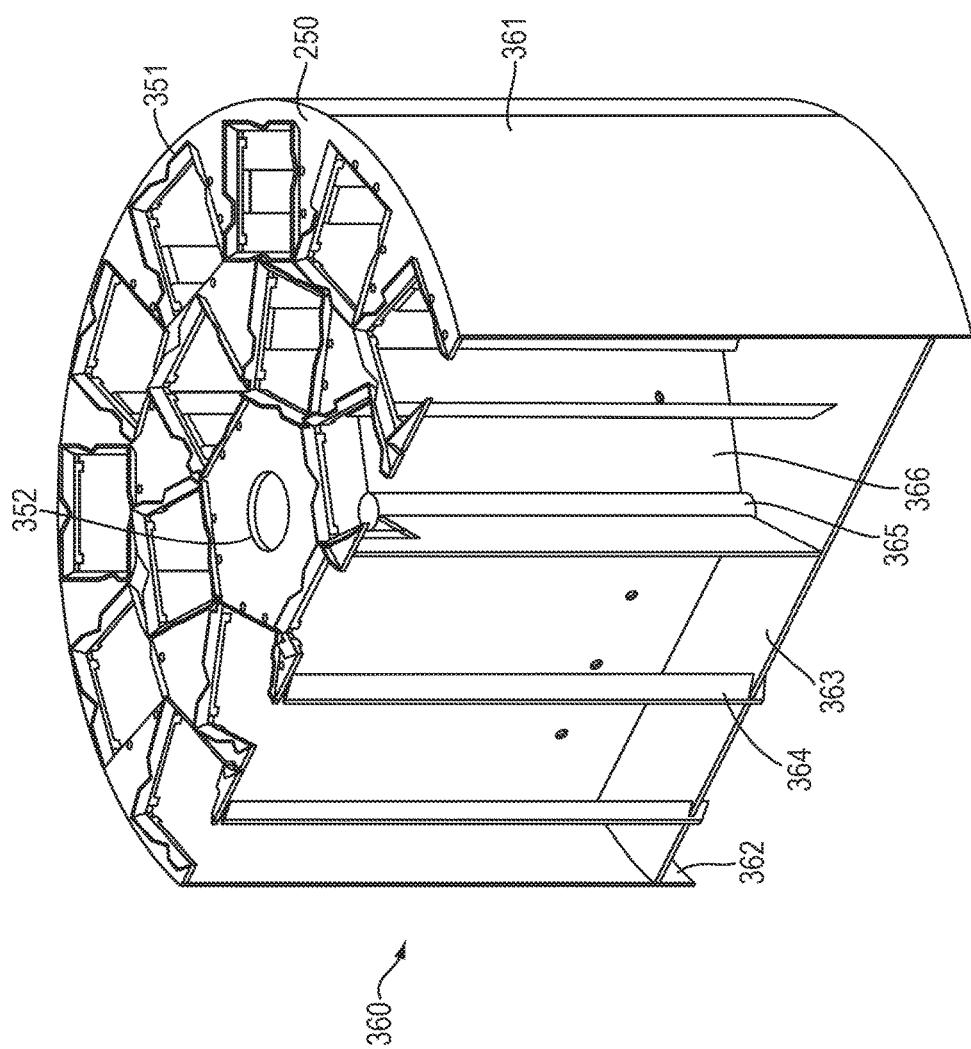
FIG. 3 is a cut-away illustration of a rack carrier and top plate in accordance with aspects of the disclosed embodiment.

FIG. 3 is a cut-away illustration of a rack carrier drum and top plate in accordance with aspects of the disclosed embodiment. FIG. 3 shows a rack carrier 360 with a top plate 250 having a plurality of rack-mounting features 351 positioned around the top plate 250. The rack carrier 360 comprises an outer wall 361 and a bottom plate 363. The outer wall 361 continues below the bottom plate 363 to a lower portion 362 configured to make contact with a pool of cryogenic fluid (not shown) resting at the bottom of the freezer 120. By contacting the cryogenic fluid, the lower portion 362 of the outer wall 361 conducts heat into the cryogenic fluid from the top plate 250 and plate 250 is a cooled thermal mass atop the rack carrier 360. The presence of the thermal mass improves the thermal storage efficiency of the rack carrier 360 by increasing heat absorption at the top of the rack carrier 360, which results in lower temperature gradients inside the rack carrier 360. Suitable configurations are shown, for example, in U.S. Pat. No. 6,393,847, entitled "Liquid Cryogen Freezer," the entire contents of which are hereby incorporated herein by reference. In preferred embodiments, the rack carrier is constructed of a material with high thermal conductivity (e.g., aluminum) to facilitate heat transfer and thermal uniformity within the freezer.

Also shown in FIG. 3, three stabilizing fins, also referred to as vertical support panels 366, radiate outward from a central shaft 365 of the rack carrier 360. The vertical support panels 366 may be affixed to the outer wall 361, lower panel 363, and the top plate 250, to increase the rigidity of the rack carrier 360. The top plate 250 may be connected to the outer wall 361 or the central shaft 365. A drive shaft opening 352 in the top plate 250 allows the drive shaft 231 to couple with the top plate 250 or the central shaft 365 of the rack carrier 360 and rotate the rack carrier 360 when the motor assembly 130 is connected to the drive shaft 231.

In operation, each rack-mounting feature 351 of the top plate 250 includes an opening sized to receive a sample storage rack (shown in FIG. 4 as 480) and support structures to position the sample storage rack in the opening and to enable each sample storage rack to hang from the top plate 250 without resting on the bottom plate 363 of the rack carrier 360, as shown in FIG. 5. Additionally, the rack carrier 360 includes support tabs 364 located adjacent to the vertical space below each rack-mounting feature 351 of the top plate 250. The support tabs 364 prevent sample trays stored in a sample storage rack adjacent the support tab from leaving the sample storage rack, and arrests the movement of the sample storage rack during rotation of the rack carrier 360.

Figure 4:
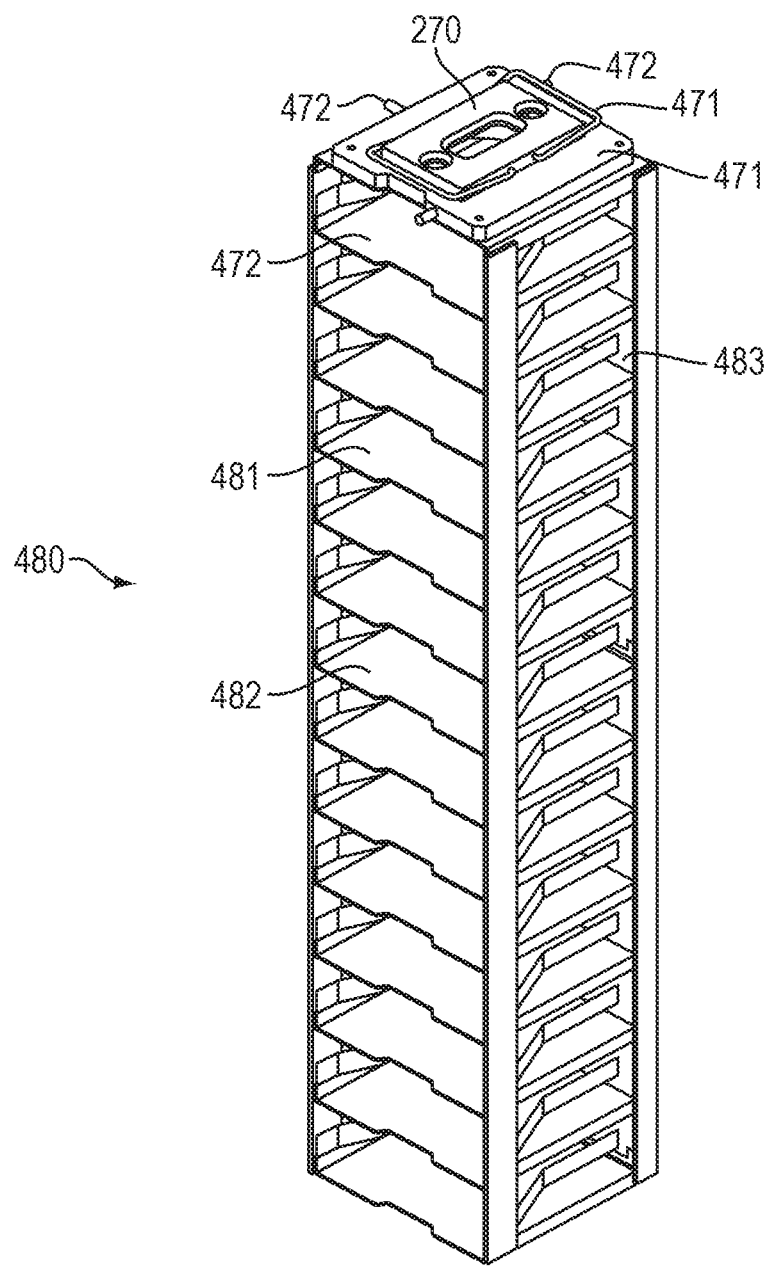
FIG. 4 is an illustration of storage rack in accordance with aspects of the disclosed embodiment.

FIG. 4 is an illustration of a storage rack in accordance with aspects of the disclosed embodiment. The sample storage rack 480 is configured to hold a plurality of sample storage trays (not shown), also referred to as storage boxes, by placing each sample storage tray on one of a plurality of vertically arranged shelves 481 spanning the length of the sample storage rack. Each shelf 481 has a pair of friction spring clips 483 configured to hold a sample storage stray (not shown) on the shelf 481. While sample storage rack 480 is illustrated as configured to hold rectangular sample storage trays (as shown, for example, in FIG. 20A-C), the sample storage racks can be configured to hold any shape sample storage trays. For example, in some embodiments, the sample storage trays and the sample storage rack have a triangular or pie-shaped horizontal cross section.

FIGS. 5A-B are illustrations of a rack carrier with the top plate securing a plurality of sample storage racks in accordance with aspects of the disclosed embodiment. FIG. 5A shows a perspective illustration of a rack carrier 360 with a portion of the outer wall 361 removed to show the arrangement of sample storage racks 480 secured to the top plate 250 of the rotatable storage drum 360. Also shown are the support tabs 364 positioned against each sample storage rack 480.

FIG. 5B shows a lower-perspective illustration of a rack carrier 360 with a portion of the outer wall 361 removed to show the arrangement of sample storage racks 480 secured to the top plate 250 of the rotatable storage drum 360. The sample storage racks 480 hang from the top plate 250 and do not contact the bottom plate 363 of the rack carrier 360. In doing so, the position of sample storage racks 480 in the rack carrier 360 is determined by the top plate 250, as shown with more detail in FIG. 6.

FIG. 6 is an illustration of the top plate of and integrated rack-mounting features of FIG. 5A showing interface between the sample storage racks 480 and the rack-mounting features in accordance with aspects of the disclosed embodiment. FIG. 6 shows a top plate of a rack carrier 360 having a plurality of rack-mounting feature 351. The rack-mounting features 351 include slanted guide fins 652 positioned to locate a sample storage rack 480 as it passes through the top plate 250. Each guide fin 652 includes a v-notch 653 or a flat-notch 654, where each notch 653, 654 is positioned to accept a pin on a sample storage rack 480. Together, two v-notches 653 constrain the sample storage rack 480 in the plane of the top plate 250, and the v-notches 653 and flat-notch 654 together constrain the position of the sample storage rack 480 in an axis orthogonal to the major plane of the top plate 250.

Figure 7:
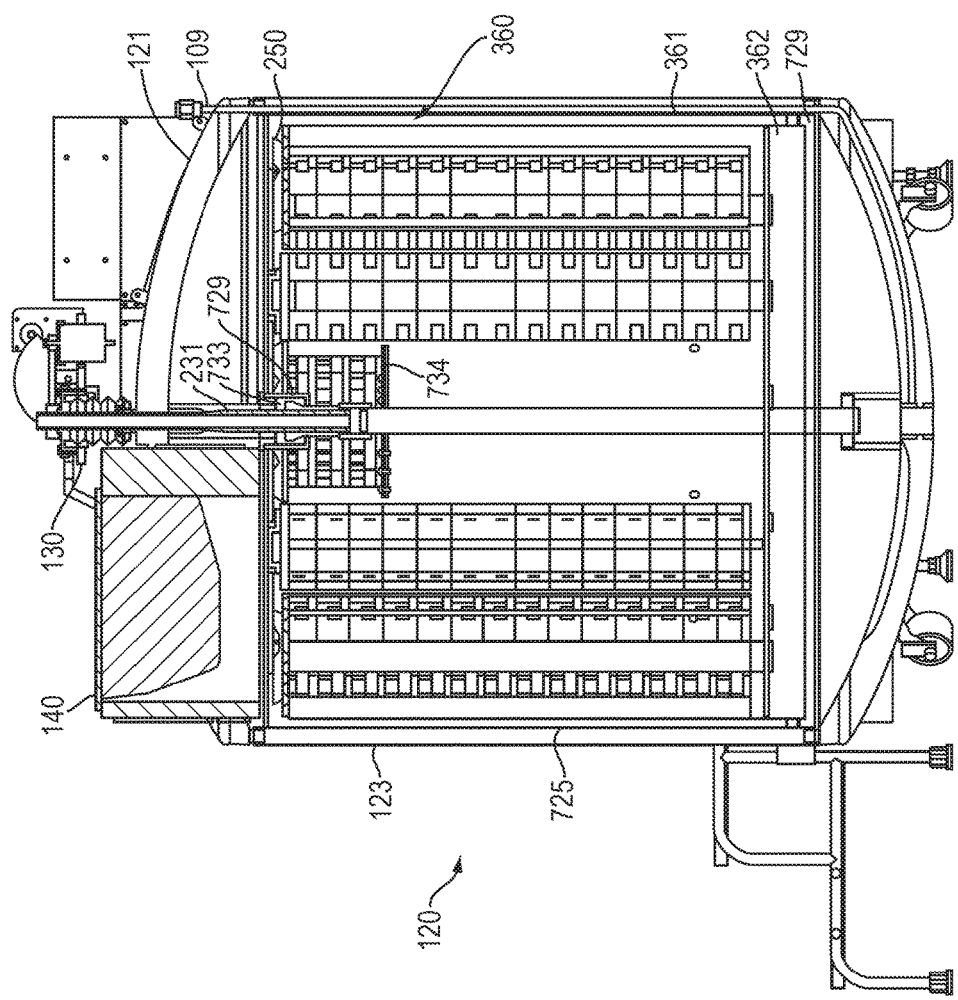
FIG. 7 is a cross-section illustration of a cryogenic storage dewar with a rack carrier coupled to a drive shaft and motor in accordance with aspects of the disclosed embodiment.

FIG. 7 is a cross-section illustration of a cryogenic storage freezer with a rack carrier coupled to a drive shaft and motor in accordance with aspects of the disclosed embodiment. FIG. 7 shows a freezer 120 in an automated-configuration with an attached motor assembly 130 and automated door 140. A rack carrier 360 is positioned inside an inner wall 725 of the freezer 120 and supported by a drive shaft 231 connected to the motor assembly 130. A refrigerant access port 109 supplies a cryogenic liquid to a bottom zone 729 of the freezer, the cryogenic fluid may pool and contact the lower portion 362 of the outer wall 361 of the rack carrier 360 to cool the top plate 250. The drive shaft 231 includes a spherical bearing 733 configured to rest against a race 729 coupled to the freezer cover 121. In a manual operation configuration, the rack carrier 360 hangs from the drive shaft 231 and is supported by the spherical bearing 733 seated against the race 729. In some embodiments, the drive shaft 231 may only be present once the freezer is configured for automatic rotation, e.g, the rack carrier 360 may be fully supported by a bearing in manual operation without the drive shaft 231. In the automated configuration shown in FIG. 7, the rack carrier 360 hangs from the drive shaft 231 and the drive shaft 231 may be supported from the motor assembly or an external drive system by, for example, a gear system.

When the freezer is constructed, a vacuum is drawn between the outer wall 123 and the inner wall 725 of the freezer 120, and the inner wall 725 may deform slightly as a result of stresses on the inner wall 725 from supporting the vacuum. A result of any deformation in the inner wall 725 is that the location of the race 729 is not precisely controlled and during manual operation, when the spherical bearing 733 of the drive shaft 231 is supporting the weight of the rack carrier 360 on the race 729, rotating the rack carrier 360 may cause precession of the long axis of the drive shaft 231. Precession of the drive shaft 231 is inconsequential during manual rotation, but could harm a motor assembly 130 attached to the drive shaft 231 by inducing stress on internal components of the motor assembly 130, and, as a result, on the assembly mounts 139 during automated rotation of the rack carrier. Additionally, automated retrieval of a sample storage rack 480 requires an automated device to mate with a sample storage rack 480 in a precise and predictable location in the freezer 120.

Continuing to refer to FIG. 7, to reduce stress on the motor assembly 130 and assembly mounts 139, and to precisely locate the sample storage rack 480 by leveling the top plate 250 in the freezer 120, the drive shaft 231 is held off the race 729 by the motor assembly 130. The assembly mounts 139 enable the motor assembly 130 to be leveled, and, as a result, the rack carrier 360 and top plate 250 are leveled inside the freezer 120. To further increase the precision of the location of the top plate 250 with respect to rotations of the drive shaft 231 by the motor assembly 130, the rack carrier 360 may be connected to the drive shaft via the top plate 250, and the top plate 250 may be directly connected to the drive shaft 231 via a connection disc 734. Without directly connecting the top plate 250 to the drive shaft 231, torque applied to the rotatable freezer 360 may twist the rotatable freezer 360 and reduce the accuracy between the position of top plate 250 and the rotation of the drive shaft 231.

Figure 8:
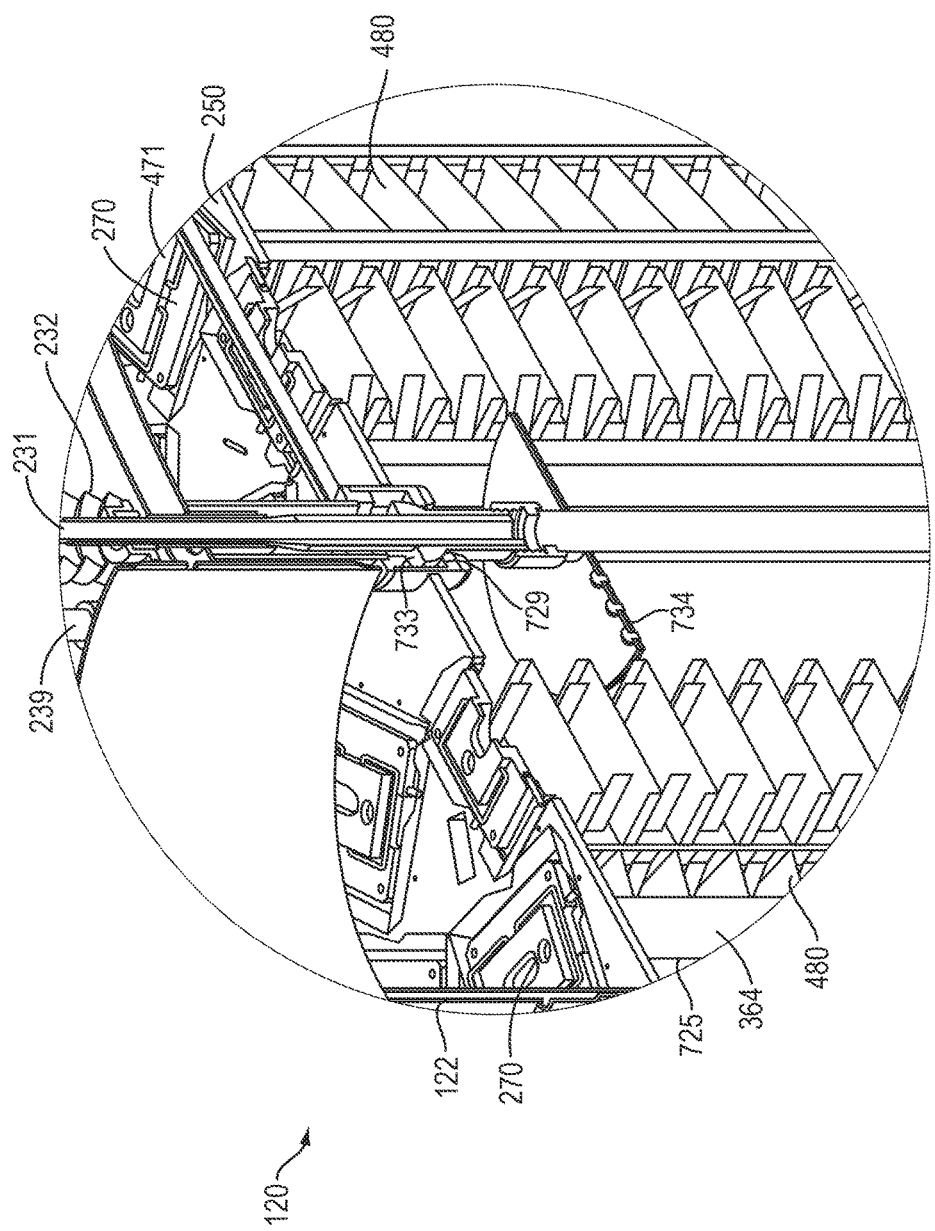
FIG. 8 is an isometric view of a cross-section of a cryogenic storage dewar with a rack carrier configured for manual operation in accordance with aspects of the disclosed embodiment.

FIG. 8 is an isometric view of a cross-section of a cryogenic storage freezer with a rack carrier configured for manual operation in accordance with aspects of the disclosed embodiment. FIG. 8 shows a freezer configured for manual access and rotation of the rack carrier 360 though the access port 122 in the freezer cover 121. The drive shaft 231 is coupled to the top plate 250 of the rack carrier 360 via the connection disc 734 and the spherical bearing 733 of the drive shaft 231 rests on the race 729. In this manner, a user reaches into the freezer 120 and rotates the rack carrier 360 by gloved hand about the race 729. Once the user has presented a desired sample storage rack 480 to the access port 122, the user retrieves the sample storage rack 480 from the freezer 120 the rack and removes the sample storage rack 480 though the access port 122.

To configure the freezer 120 for automated rotation and retrieval of the sample storage racks 480, a motor assembly is attached to the motor mounts 239 and the drive shaft 231. To lift the spherical bearing 733 off of the race 729, the drive shaft may include a threaded exterior end (shown in FIG. 9 as 934). The threaded exterior end of the drive shaft 231 enables rotation of the rack carrier 360 to thread the drive shaft 231 into the motor assembly 130 and lift the spherical bearing 733 off the race 729. Once lifted, the drive shaft 231 may be locked into position in the motor assembly 130 to prevent further threading or de-threading of the drive shaft 231.

Figure 9:
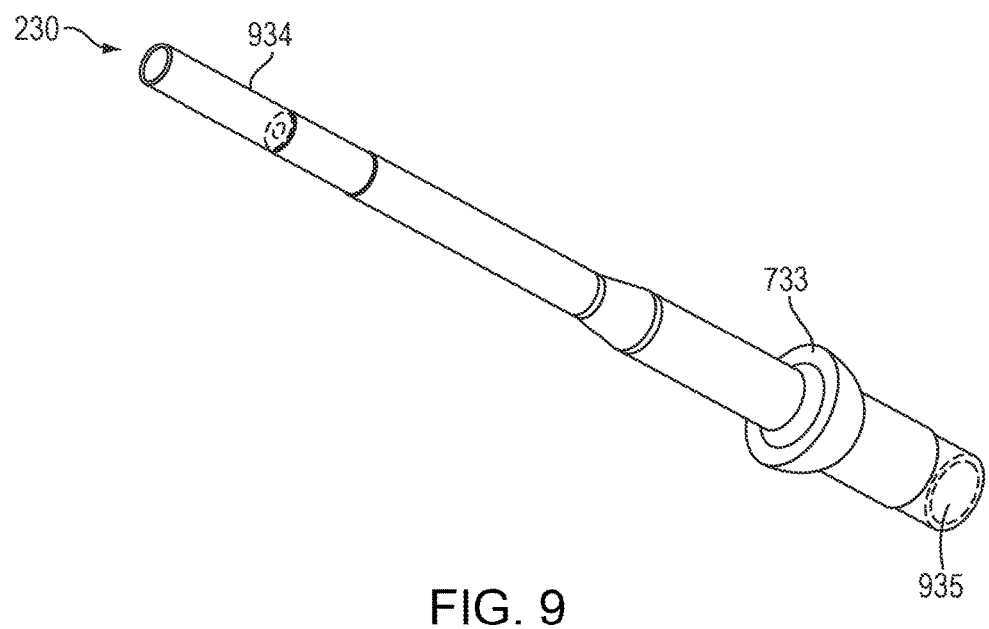
FIG. 9 is an illustration of the drive shaft of FIGS. 7 and 8 in accordance with aspects of the disclosed embodiment.

FIG. 9 is an illustration of the drive shaft of FIGS. 7 and 8 in accordance with aspects of the disclosed embodiment. FIG. 9 shows a drive shaft 230 including a threaded exterior end 934 adapted to be threaded into a motor assembly 130, an interior end 935 adapted to be coupled to a connection disc 734 or directly coupled to the top plate 250, and a spherical bearing 733.

Figure 10A:
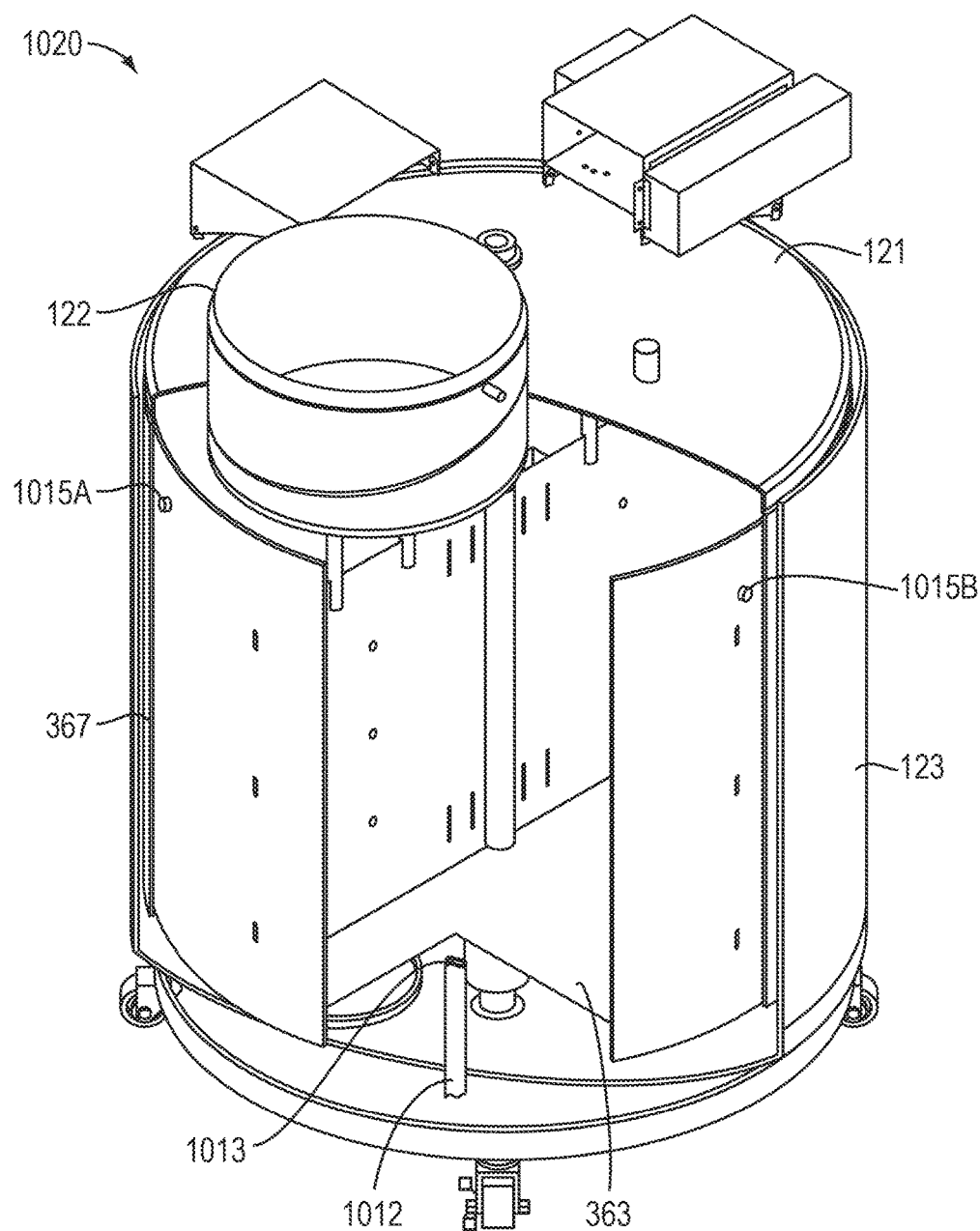
FIGS. 10A-C are illustrations of freezers having respective rack carriers mounted in alternative configurations in accordance with further embodiments.
Figure 10B:
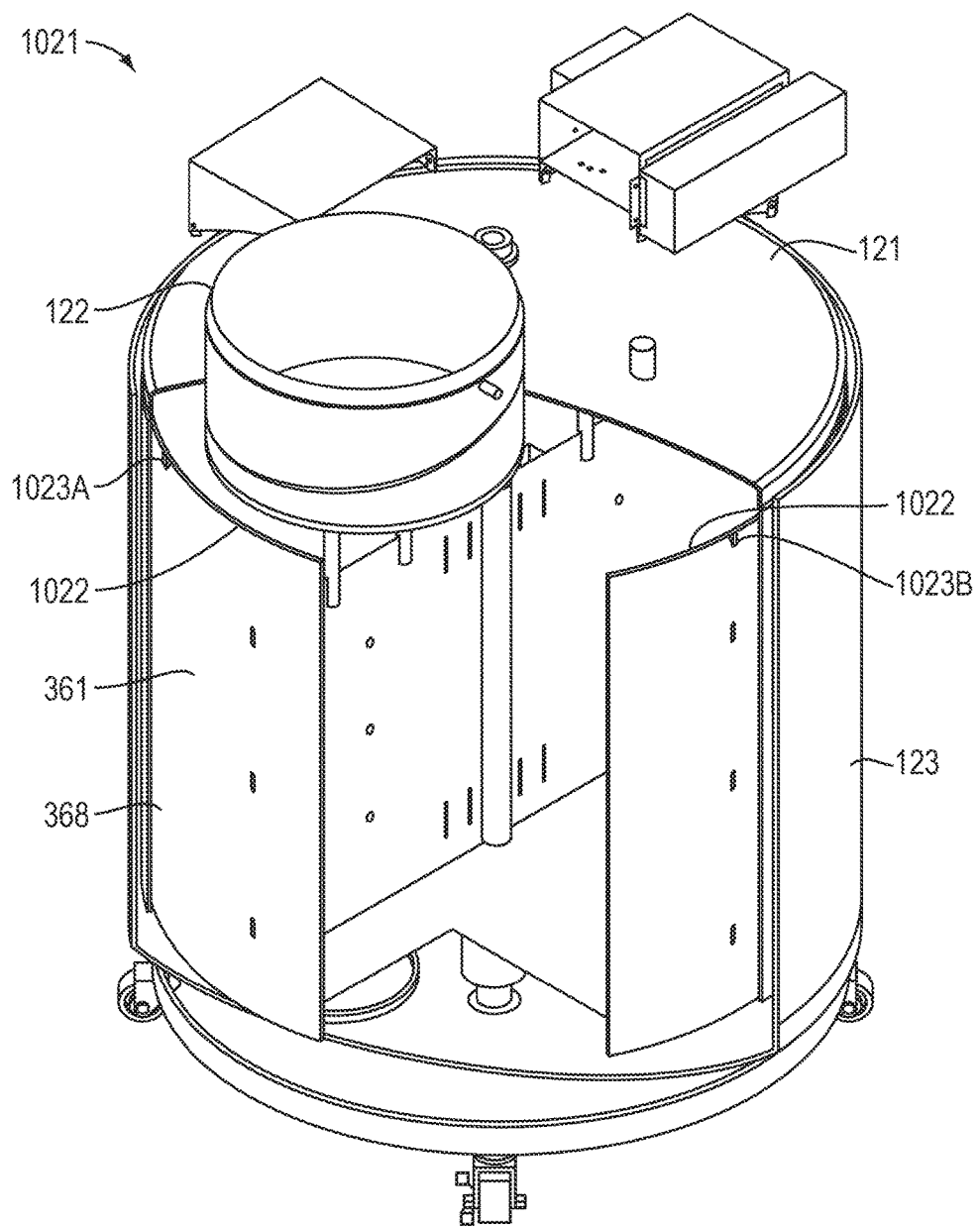
Figure 10C:
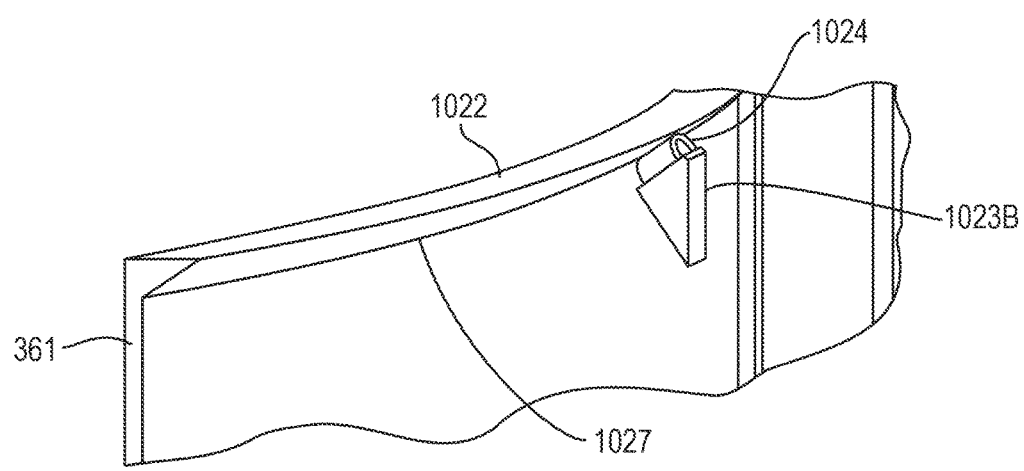

FIGS. 10A-C are illustrations of freezers having respective rack carriers mounted in alternative configurations in accordance with further embodiments. As described above with reference to FIGS. 1-9, the rack carrier 360 may be supported within the freezer 120 by the drive shaft 231, which connects to the top plate 250 of the rack carrier 360 via the connection disc 734 at the center of the rack carrier 360. In further embodiments, a rack carrier may be supported within a freezer by other means, such as supporting apparatus connected at a bottom portion of the rack carrier or at a circumference of the rack carrier.

FIG. 10A illustrates a freezer 1020 housing a rack carrier 367. The freezer 1020 may be configured to incorporate features of the freezer 120 described above with reference to FIGS. 1-9, including the external wall 123, freezer cover 121, and access port 122. The rack carrier 367 may be configured to incorporate features of the rack carrier 360 described above, including the bottom plate 363. In contrast to the rack carrier 360, the rack carrier 367 is supported, at least in part, by one or more pillars, including a pillar 1012, extending from the bottom of the freezer 1020 and contacting the bottom plate 363 of the rack carrier. The pillar 1012 may contact the bottom plate 363 via a wheel 1013 (also referred to as a bearing member) or, alternatively, another apparatus that enables rotation of the rack carrier 367 with minimal friction (e.g., one or more ball bearings). Although only a single pillar 1012 is shown, a plurality of pillars or other support structures may be implemented as required to adequately support some or all of the weight of the rack carrier 367. Alternatively, the pillars may be mounted to the bottom surface of the bottom plate 363, and the respective wheels may instead make contact with a floor of the freezer 1020.

Further, a plurality of spacers 1015A-B may be positioned between the outer wall of the rack carrier 367 and the inner wall of the freezer 1020. The spacers 1015A-B contribute to maintaining the position of the rack carrier 367, and can be fixed to either the rack carrier 367 or the inner wall of the freezer 1020. The spacers 1015A-B may include one or more wheeled or ball-bearing members (not shown) located opposite the point of attachment to facilitate rotation of the rack carrier 367.

FIG. 10B illustrates a freezer 1021 housing a rack carrier 368. The freezer 1021 may be configured to incorporate features of the freezer 120 described above with reference to FIGS. 1-9, including the external wall 123, freezer cover 121, and access port 122. The rack carrier 368 may be configured to incorporate features of the rack carrier 360 described above. In contrast to the rack carrier 360, the rack carrier 368 includes a lip 1022 at the top portion of the outer wall 361. The lip 1022 extends outward from the outer wall 361 at the top and along the circumference of the outer wall 361, and contacts a plurality of lip mounts 1023A-B fixed to the inner wall of the freezer 1021. The weight of the rack carrier 368 may be supported, at least in part, by the lip mounts 1023A-B. Although two lip mounts 1023A-B are shown, additional lip mounts may be located at the inner wall of the freezer 1021 as required to support the rack carrier 368.

FIG. 10C illustrates an inset view of the freezer 1021 to depict the lip 1022 and a lip mount 1023B in further detail. Here, it can be seen that the lip 1022 extends outward from the outer wall 361 to provide an angled surface 1027 at the underside of the lip 1022. This surface 1027 may generally align with a top surface of the lip mount 1023B, which contacts the surface 1027 via a wheel 1024 (also referred to as a bearing member). The wheel 1024 enables the surface 1027 to move along the lip mount 1023B with minimal friction, facilitating rotation of the rack carrier 368. Alternatively, another apparatus, such as one or more ball bearings, may be implemented in place of the wheel 1024 to enable rotation of the rack carrier 367.

The freezer configurations described above with reference to FIGS. 10A-C may accommodate driving the rack carrier 367/368 via a central shaft, as described above with reference to FIGS. 1-9. If configured for automation, the rack carrier 367/368 may be lifted off of the respective supports (e.g., pillar 1012, lip mounts 1023A-B) to engage with the central drive shaft connected to the automation system (e.g., system 105). In such a configuration, the central shaft may support substantially all of the weight of the rack carrier 367/368. Alternatively, the rack carrier 367/368 may maintain contact (and be at least partially supported by) the respective supports (e.g., pillar 1012, lip mounts 1023A-B).

In still further embodiments, the rack carrier 367/368 may be driven by a non-central drive assembly. In such an embodiment, a central shaft may be implemented to support some or all of the weight of the rack carrier 367/368. However, a motor drive (comparable to the motor assembly 130 described above) may be configured to engage with the rack carrier 367/368 at a location other than the central shaft, such as along the periphery of the rack carrier 367/368. Example configurations for a non-central drive system include: 1) a bevel gear assembly, where a drive gear is oriented perpendicular to a gear on the rack carrier, and may be located on the periphery of the rack carrier, and a carrier gear may run around an outside upper portion of the rack carrier; 2) a spur gear assembly, where a drive gear is set on the periphery of the rack carrier and the carrier gear may run around the outside upper portion of the rack carrier; 3) a friction drive assembly, where a drive wheel acts against a surface of the upper part of the rack carrier (either the top or side of the rack carrier).

Figure 11A:
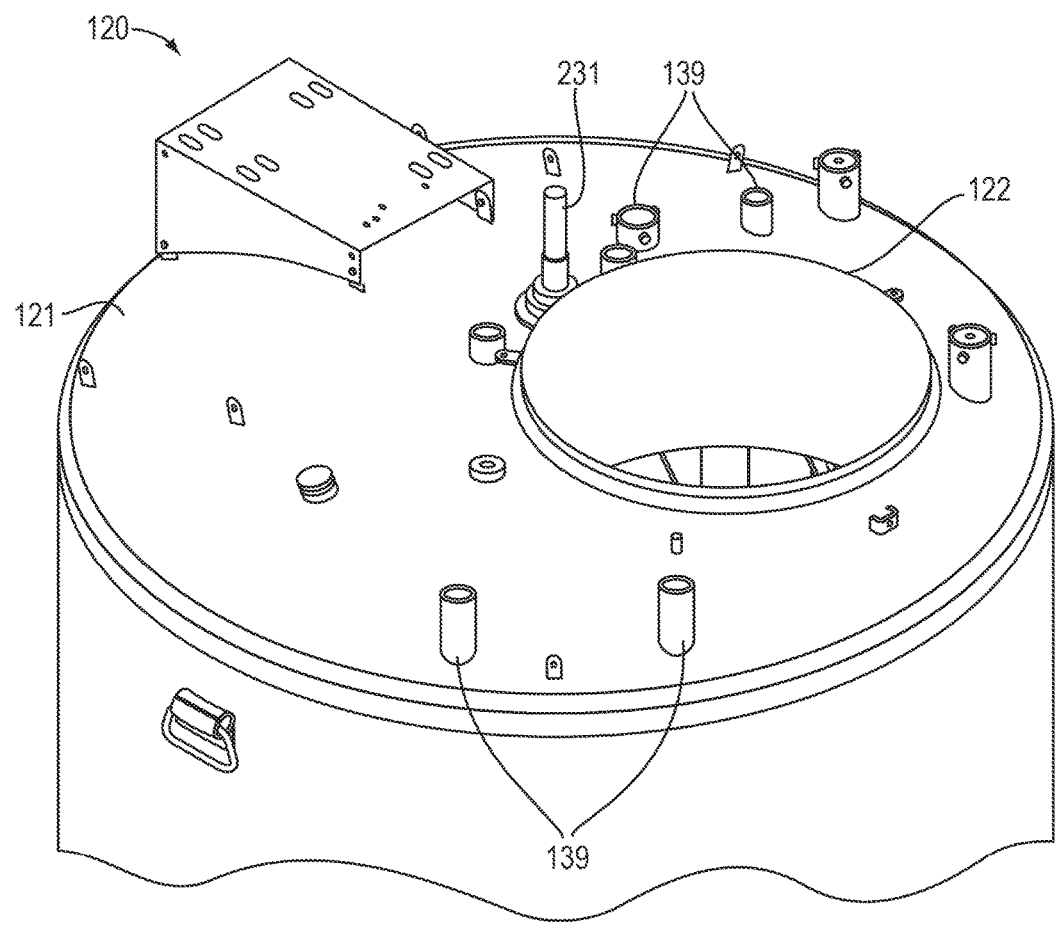
FIGS. 11A-G are illustrations of a top portion of a freezer during a process of installing mounting hardware in accordance with aspect of the disclosed embodiment.

FIGS. 11A-G illustrate a top portion of a freezer 120 during a process of installing mounting hardware in accordance with aspect of the disclosed embodiment. As shown in FIG. 11A, the freezer cover 121 accommodates the access port 122, drive shaft 231 and a number of assembly mounts 139 (also referred to as mounting posts), as described above. The assembly mounts 139 can be used to mount the automation system 105, described above with reference to FIG. 1, to the freezer 120, or may be used to mount other features to the freezer 120. However, the process of mounting the automation system 105 to the freezer 120 may encounter a number of challenges. For example, the location of the assembly mounts 139 may vary among different freezers. Further, the mounts 139 may be fixed to the freezer cover prior to pulling a vacuum on the freezer cover 121. The process of pulling the vacuum can deform the top surface of the freezer cover 121, relocating the assembly mounts 139. Without a process to ensure the automation system 105 is mounted at a precise relation to the access port 122 and the drive shaft 231, the automation system 105 may encounter difficulty in operating to retrieve and replace samples within the freezer 120.

A process, described below with reference to FIGS. 11B-G, provides for installing mounting hardware having a precise relation to the access port 122, thereby enabling the automation system 105 or other features to be mounted accurately to the freezer 120.

Figure 11B:
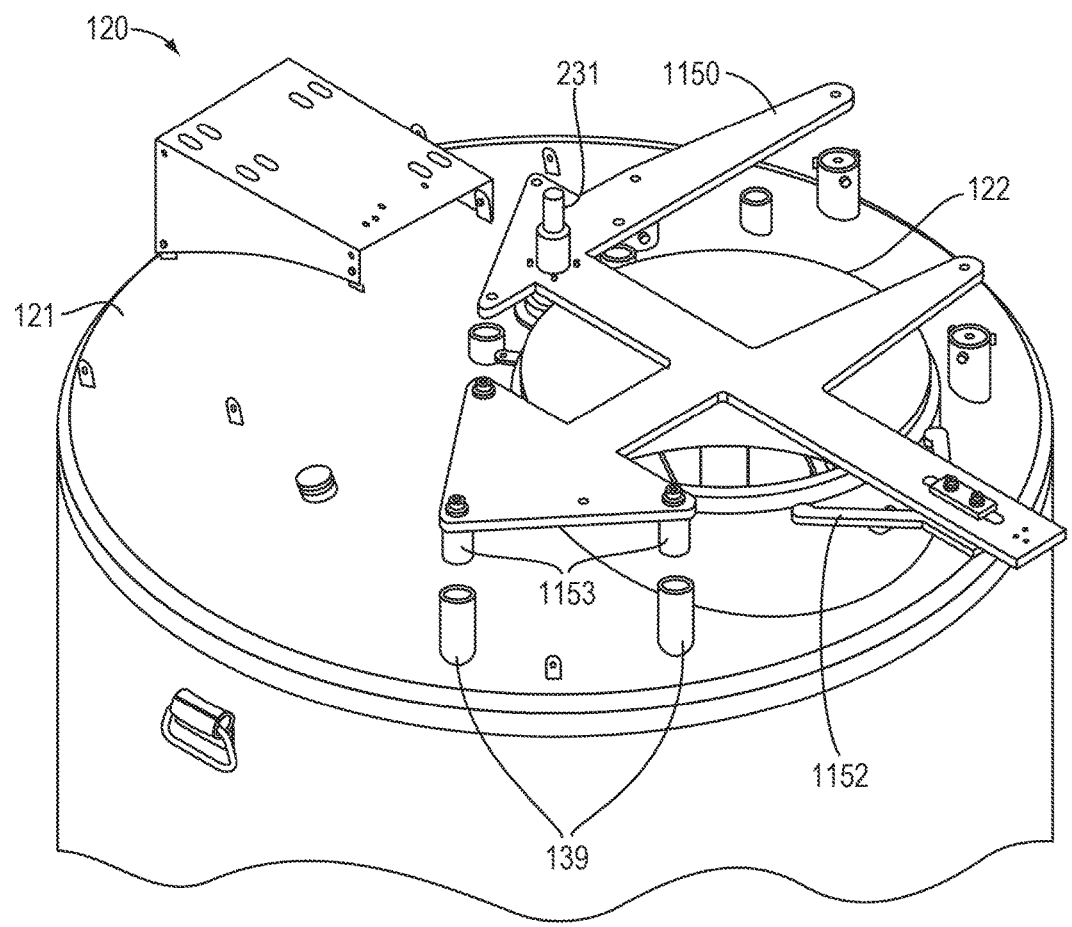

1) Weld the assembly mounts 139 to the top surface of the freezer cover 121. As shown in FIG. 11B, a guideplate 1150 is placed above the access port 122. The guideplate 1150 includes a number of locating features that are aligned so as to indicate the appropriate locations for the mounting hardware to be installed. In particular, the guideplate 1150 can include protrusions 1153 that are to be aligned with the assembly mounts 139 to be welded. In order to properly align the guideplate 1152 to the access port 122 and the driveshaft 231, the guideplate 1150 can include a bracket 1152 to contact the side of the access port 122, as well as an aperture to accommodate the drive shaft 231.

2) Pull the vacuum on the freezer cover 121. An internal chamber (not shown) of the freezer cover may be accessed via a port and evacuated. As indicated above, this operation may alter the positions of the assembly mounts 139.

Figure 11C:
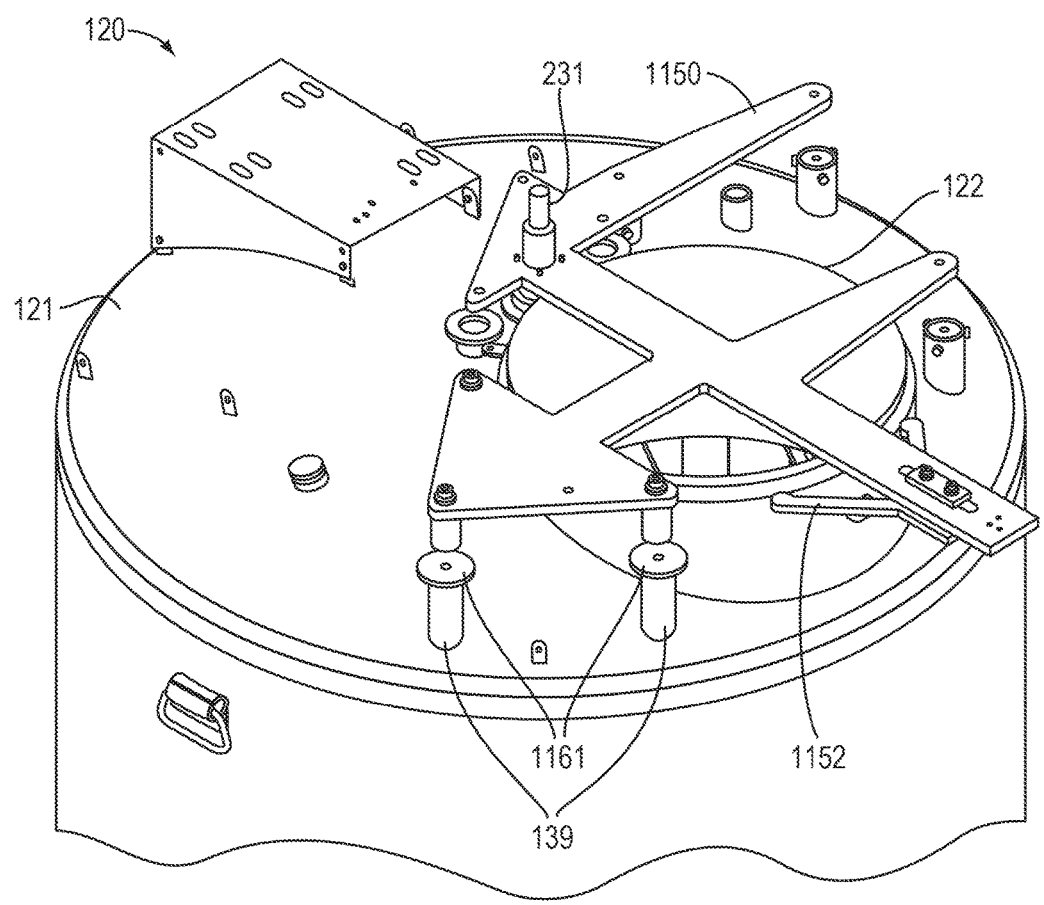

3) Position the washers 1161 on top of assembly mounts 139. As shown in FIG. 11C, the guideplate 1150 also indicates the appropriate position of the washers 1161.

Figure 11D:
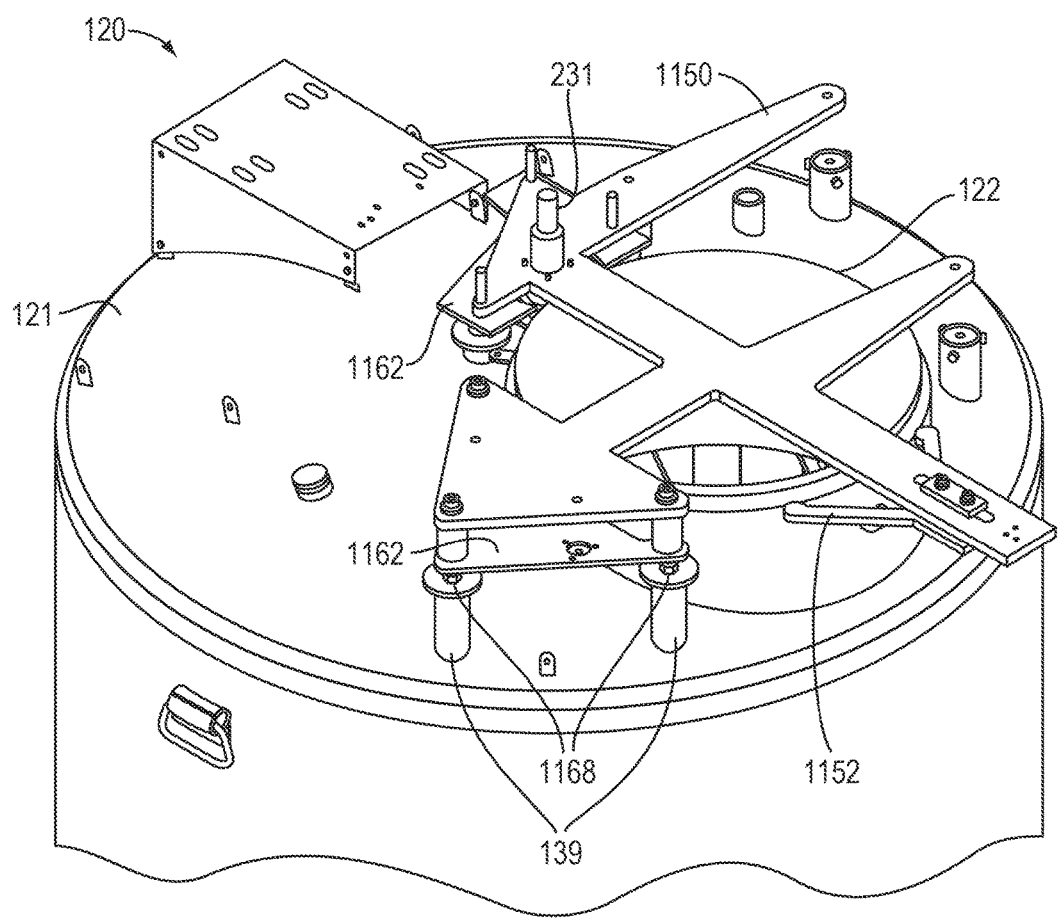

4) Install the mounting plates 1162 above the washers 1161. As shown in FIG. 11D, the guideplate 1150 guides the position of the mounting plates 1162 during installation. Studs 1168 are positioned through the washers 1161 to connect with the mounting plates 1162. The studs 1168 may be adapted to allow the mounting plates 1162 limited movement in three dimensions to ensure the mounting plates 1162 are properly aligned with the guideplate 1150. As a result, the guideplate 1150 can ensure the correct location of the mounting plates 1162 regardless of any variations in the freezer cover 121. The mounting plates 1162 may be held on the guideplate 1150 and then fixed to the washers 1161 via the studs 1168.

Figure 11E:
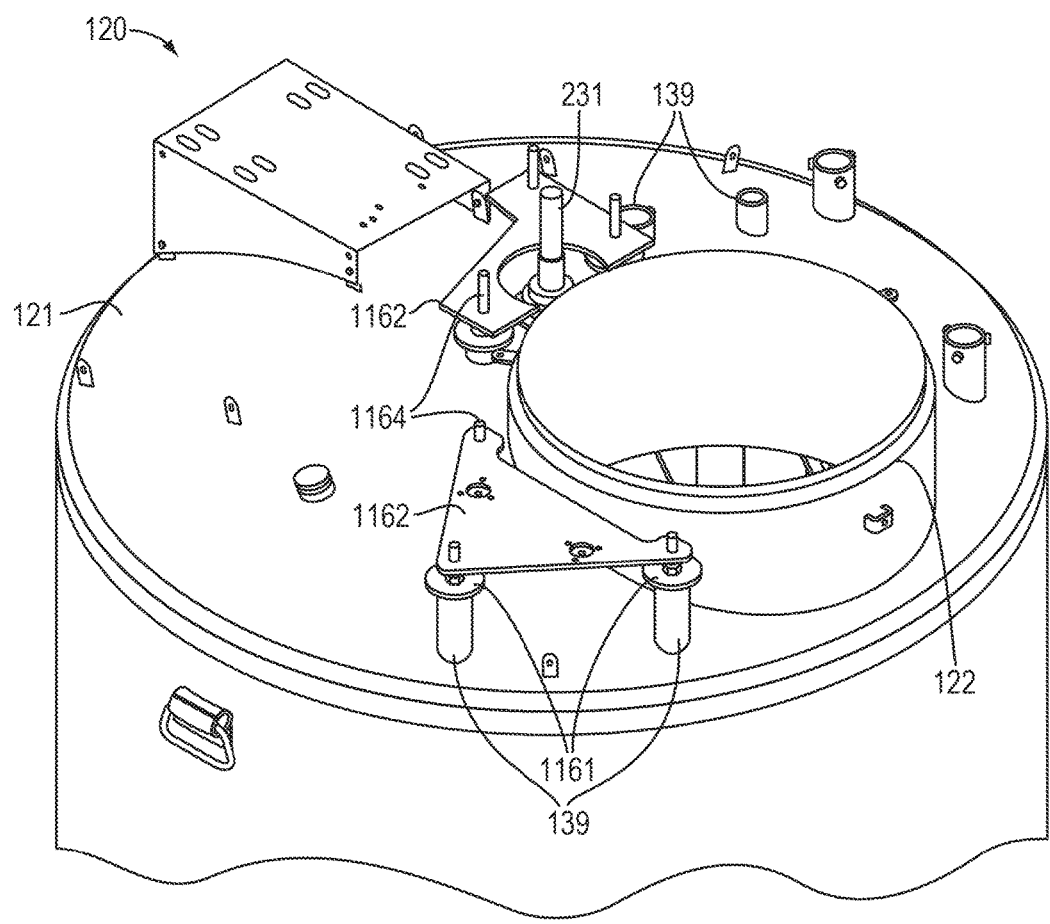

5) Weld the washers 1161 and studs 1168 in place. With the guideplate 1150 ensuring the correct position of the washers 1161 via the mounting plates 1162 as shown in FIG. 11D, the washers 1161 may then be welded to the assembly mounts 139. With the guideplate 1150 removed, as shown in FIG. 11E, the mounting plates 1160 may include (or be affixed to) mounting pins 1164, which may accommodate apertures of the guideplate 1150 as well as features of the assembly to be mounted to the freezer 120.

Figure 11F:
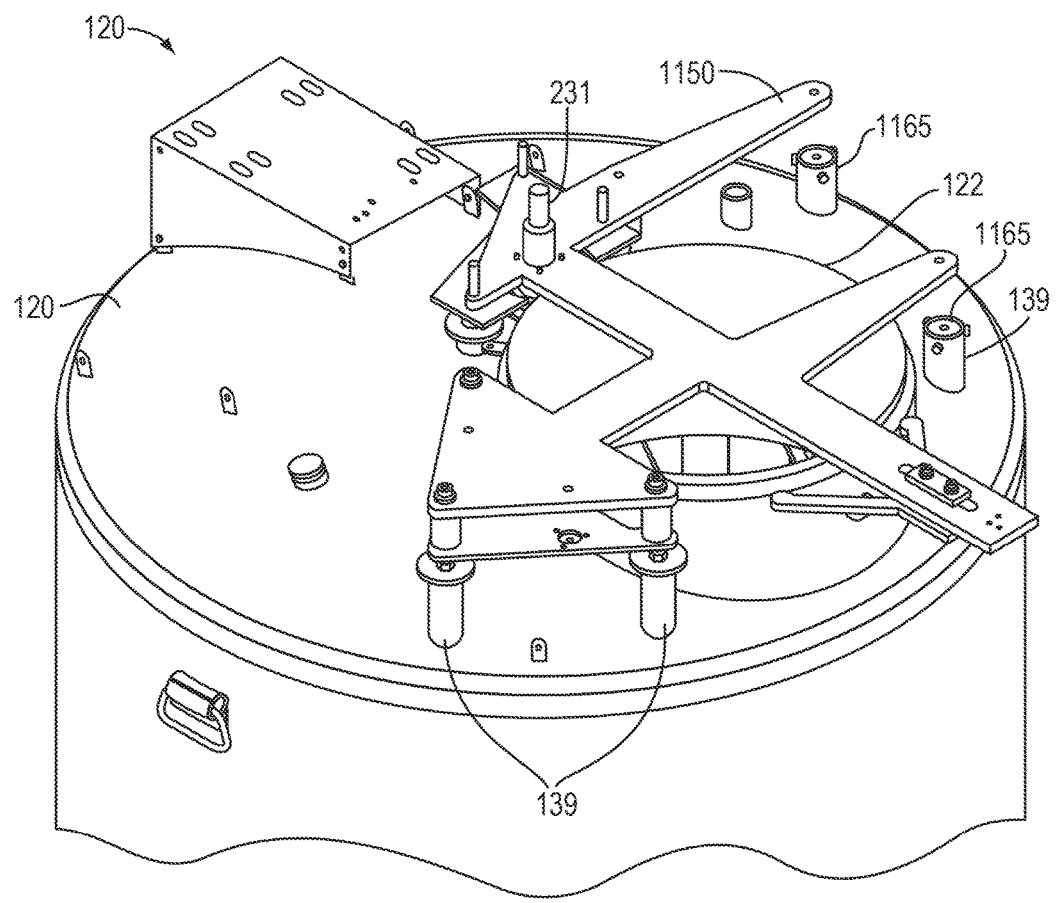
Figure 11G:
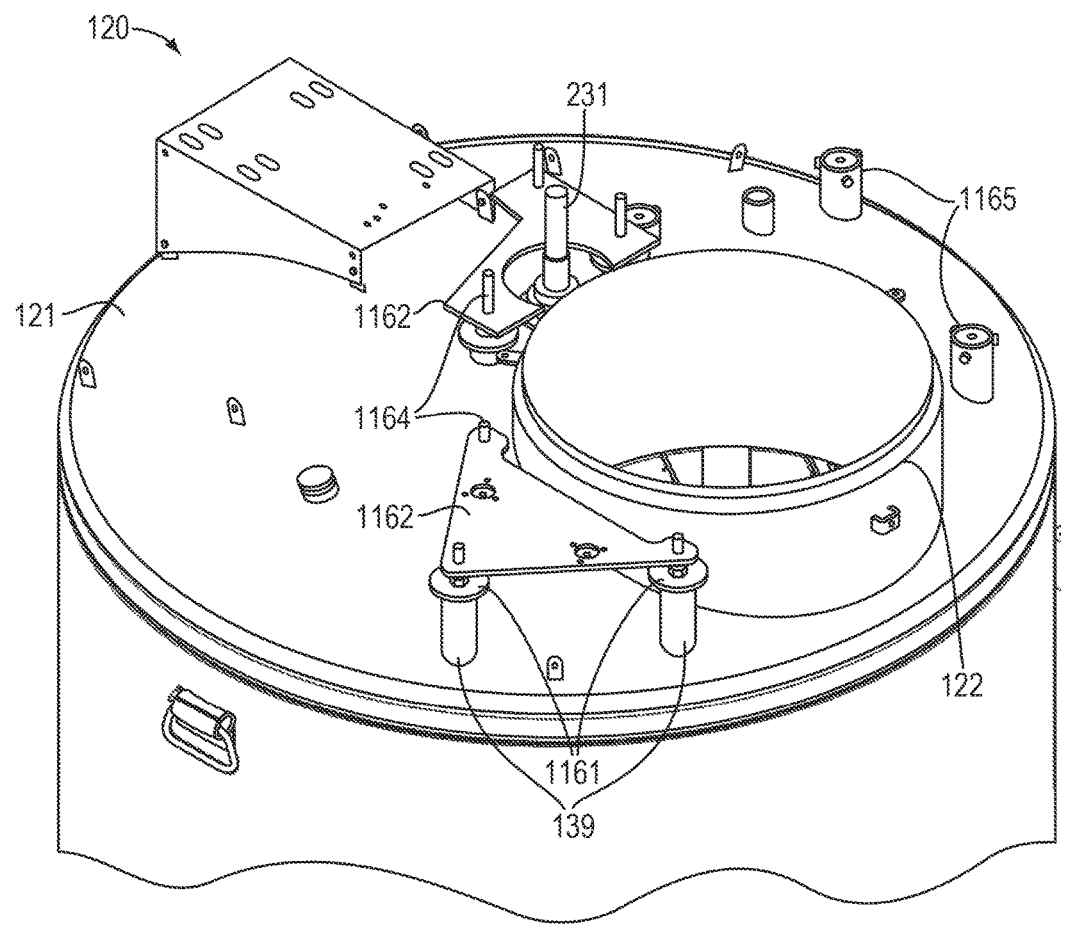

6) Install mounting discs 1165 to the top of selected assembly mounts 139. As shown in FIG. 11F, the mounting discs 1165 can be fixed to some of the assembly mounts 139 to accommodate particular features of the automation system 105 or other assembly. The guideplate 1150 may also include locating holes or other features that can be implemented to install other mounting features, such as location holes (e.g., at the top of mounting discs 1165) or locating pins. The mounting plates 1160 may include removable inserts at the locations receiving location holes. As a result, if an error is made in drilling a location hole, the removable inserts may be replaced and re-drilled. The mounting discs 1165 may also be removed and replaced for the same reason. The completed freezer cover 121, including all mounting hardware installed, is illustrated in FIG. 11G.

Further details of suitable motor assemblies and retrieval modules for use with the invention described herein can be found in the provisional patent application 62/140,157, entitled "Automated Cryogenic Storage System," filed on Mar. 30, 2015, and now filed as a U.S. Utility Application on Mar. 30, 2016, the entirety of which is incorporated herein by reference.

While this invention has been particularly shown and described with references to example embodiments thereof, it will be understood by those skilled in the art that various changes in form and details may be made therein without departing from the scope of the invention encompassed by the appended claims.

What is claimed is:

1. A cryogenic storage device comprising:
   a freezer configured to maintain a cryogenic environment, the freezer comprising:
      a port enabling access to the cryogenic environment through a top portion of the freezer;
      a rack carrier having a plurality of rack-mounting features at a top surface of the rack carrier, each of the rack-mounting features being configured to accept a sample storage rack through the top surface and to position an end of the sample storage rack, the sample storage rack being configured to store a plurality of sample storage trays;
      a bearing including a bearing member coupled with the rack carrier and a stationary race coupled to the freezer, the bearing configured to support the rack carrier when the stationary race is coupled with the bearing member; and
      a shaft interface including a shaft extending though at least a portion of the freezer, the shaft having an exterior portion and an interior portion coupled to the rack carrier, the shaft configured to drive vertical translation of the rack carrier to decouple the rotating bearing member from the stationary race, the shaft supporting the rack carrier when the rotating bearing member is decoupled from the stationary race.

2. The cryogenic storage device of claim 1, wherein the cryogenic storage device includes a manual rotation configuration and an automated rotation configuration, the rack carrier resting on the bearing in the manual rotation configuration and the rack carrier hanging from the drive shaft coupled to a motor assembly in the automated rotation configuration.

3. The cryogenic storage device of claim 2, wherein, in the automated rotation configuration, the motor assembly supports a weight of the rack carrier via the drive shaft and the motor assembly is configured to rotate the rack carrier.

4. The cryogenic storage device of claim 3, wherein the exterior end of the drive shaft includes threads adapted to screw the drive shaft into corresponding threads in the motor assembly, and wherein threading the drive shaft into the corresponding threads in the motor assembly vertically translates the rack carrier.

5. The cryogenic storage device of claim 1, wherein the sample storage rack hangs on the rack carrier.

6. The cryogenic storage device of claim 1, further including a volume of cryogenic liquid inside the freezer, a lower portion of the rack carrier extending into the volume of cryogenic liquid, the carrier comprising a thermal conductor from a lower portion the rack carrier to the rack-mounting features.

7. The cryogenic storage device of claim 1, wherein the rack-mounting features are coupled to the interior end of the drive shaft.

8. The cryogenic storage device of claim 1, wherein the bearing member is integrated with the drive shaft.

9. The cryogenic storage device of claim 1, wherein an exterior surface of the top portion of the freezer includes motor assembly mounts adapted to secure the motor to the freezer, the motor assembly mounts supporting the weight of a motor assembly and the rack carrier when the cryogenic storage device is in the automated configuration.

10. The cryogenic storage device of claim 9, wherein the motor assembly mounts enable leveling of the motor assembly and the rack carrier when the rack carrier is coupled to the motor assembly.

11. The cryogenic storage device of claim 1, wherein an exterior surface of the top portion of the freezer includes at least one mounting feature adapted to secure a retrieval module, the retrieval module configured to access the freezer and retrieve the sample storage rack through the port.

12. The cryogenic storage device of claim 1, wherein each corresponding opening of the plurality of rack-mounting features includes guide fins surrounding the corresponding opening to guide a bottom end of one of the plurality of sample storage racks when the sample storage rack is lowered through the corresponding opening of the top plate.

13. The cryogenic storage device of claim 1, wherein the bearing member is a rotating bearing member.

14. The cryogenic storage device of claim 1, wherein the bearing member includes a plurality of bearing members affixed to an inner wall of the freezer.

15. The cryogenic storage device of claim 1, wherein the bearing member includes a plurality of bearing members affixed to a bottom inner surface of the freezer, the bearing members being positioned to contact a bottom plate of the rack carrier.

16. The cryogenic storage device of claim 1, wherein the shaft is a drive shaft, the drive shaft having an exterior portion configured to be coupled to a motor assembly.

17. A cryogenic storage device comprising:
   a freezer configured to maintain a cryogenic environment, the freezer comprising:
      a port enabling access to the cryogenic environment through a top portion of the freezer;
      a volume of cryogenic fluid inside the freezer, the volume of cryogenic fluid pooling on a bottom surface of the inside of the freezer;
      a rack carrier inside the freezer, the rack carrier including a plurality of rack-mounting features at a top surface of the rack carrier, each of the rack-mounting features being configured to accept a sample storage rack through the top surface and precisely position an end of the sample storage rack, the sample storage rack being configured to store a plurality of sample storage trays; and
      a lower portion the rack carrier extending into the volume of cryogenic liquid, the carrier comprising a thermal conductor from a lower portion the rack carrier to the rack-mounting features.

18. The cryogenic storage device of claim 17, wherein the plurality of sample storage racks hang from the rack-mounting features.

19. A method of converting a manual operation freezer into an automated operation freezer, the method comprising:
   providing a freezer having a drive shaft though a top portion of the freezer and a rack carrier positioned inside of the freezer, the rack carrier resting on a bearing and adapted to be supported by the drive shaft, the rack carrier having a plurality of rack-mounting features at a top surface of the rack carrier, each of the rack-mounting features being configured to accept a sample storage rack through the top surface and to position an end of the sample storage rack, the sample storage rack being configured to store a plurality of sample storage trays,
attaching a motor assembly to an exterior surface of the top portion of the freezer;
lifting the rack carrier off the rotating bearing using the drive shaft, the lifting causing the rack carrier to be supported by the drive shaft; and
securing the drive shaft to the motor assembly.

20. The method of claim 19, wherein the drive shaft includes a threaded exterior end, and lifting the rack carrier off the rotating bearing using the drive shaft further includes threading the threaded exterior end of the drive shaft into a corresponding threaded opening in the motor assembly, the threading lifting the rack carrier off the rotating bearing.

21. The method of claim 20, threading the threaded exterior end of the drive shaft into a corresponding threaded opening in the motor assembly further includes manually rotating the rack carrier through a door in the top portion of the freezer.

22. The method of claim 20, further including supporting the rack carrier with the motor assembly.

* * * * *